United States Patent [19]

Burks

[11] Patent Number: Plant 7,236

[45] Date of Patent: May 29, 1990

[54] ROSE PLANT NAMED BURALP

[75] Inventor: Larry J. Burks, Rte. 22, Box 289, Tyler, Tex. 75704

[73] Assignee: Larry J. Burks, Tyler, Tex.

[21] Appl. No.: 321,721

[22] Filed: Mar. 10, 1989

[51] Int. Cl.[5] ..... A01H 5/00

[52] U.S. Cl. ..... Plt./21

[58] Field of Search ..... Plt. 20, 21

*Primary Examiner*—Howard J. Locker

*Attorney, Agent, or Firm*—Christie, Parker & Hale

[57] ABSTRACT

A new and unusual deep red hybrid tea rose.

1 Drawing Sheet

SUMMARY OF THE INVENTION

The present invention relates to a new and distinct variety of rose plant of the hybrid tea rose class, which was originated by my crossing as seed parent the variety known as "Poinsettia" and as pollen parent the rose known as "National Beauty". The varietal denomination of this new rose is "Buralp".

Among the novel characteristics possessed by this new variety which distinguish it from its parents and all other varieties of which I am aware are its deep red flowers in this class of rose. Flowers are long lasting on the plant and after cutting. Asexual reproduction by budding of the new variety as performed in Smith County, Tex., shows that the foregoing and other distinguishing characteristics come true to form and are established and transmitted through succeeding propagations.

BRIEF DESCRIPTION OF DRAWING

The accompanying drawing shows typical specimens of the vegetative growth and flowers of the new variety in different stages of development depicted in color as nearly true as it is reasonably possible to make the same in a color illustration of this character.

DESCRIPTION OF PREFERRED EMBODIMENT

The following is a detailed description of my new variety, with color terminology in accordance with The Royal Horticultural Society Colour Chart (R.H.S.C.C.). The terminology used in color description herein refers to plate numbers in the aforementioned color chart, e.g., "46A" is plate 46A of The Royal Horticultural Society Colour Chart.

Parentage: Seedling.

*Seed parent.*—"Poinsettia".

*Pollen parent.*—"National Beauty".

Class: Hybrid Tea.

The following observations are made of specimens grown outdoors in Smith County, Texas, during the month of October.

FLOWER

Blooming habit: Nearly continuous.

A. Bud:

(1) *Size.*—Medium.

(2) *Form.*—Pointed.

(3) *Color.*—As sepals divide, bud color is near 184A.

(4) *Sepals.*—Longer than bud, foliated.

(5) *Peduncle.*—Length — long. Aspect — straight, heavy. Strength — erect. Color — near 183C.

B. Bloom:

(1) *Size.*—Average size when fully expanded — about 4½ inches.

(2) *Borne.*—Singly, one to a stem.

(3) *Form.*—High centered at first, becoming flat. Outer petals roll under.

(4) *Petalage.*—Number of petals under normal conditions — about 35.

(5) *Color.*—After sepals fall and petals unfurl, predominant flower color viewing petals' top surface is near 46A with near 202A edging on some petals. Petal undersurface is near 43B. Color at point of petal attachment is near 44A. Blooms may lighten somewhat upon aging, to near 46B but generally color holds well through maturity.

C. Petals:

(1) *Texture.*—Thick.

(2) *Appearance.*—Inside velvety and outside satiny.

(3) *Form.*—Broad, fan shaped.

(4) *Arrangement.*—Regularly arranged, imbricated.

(5) *Petaloids in center.*—Few.

(6) *Persistence.*—Average.

(7) *Fragrance.*—Slight.

(8) *Lasting quality.*—Very long lasting quality on plant and as cut flower.

REPRODUCTIVE ORGANS

A. Stamens, filaments and anthers:

(1) *Arrangement.*—Regularly arranged around styles, abundant.

(2) *Color.*—Filaments orange.

B. Pollen:

*Color.*—Yellow.

C. Styles: Even, medium length.

D. Stigmas:

*Color.*—Ivory, cream.

E. Hips: Globular, medium size, orange to orange red color, seeds do not protrude.

PLANT

A. Form: Upright.

B. Growth: Vigorous.

*Height attained.*—About 5 feet.

C. Foliage: Compound 5.

(1) *Size.*—Medium to large.

(2) *Quantity.*—Abundant.

(3) *Color.*—New foliage: Upper side — purplish. Under side — purplish green. Old foliage: Upper side — near 146A. Under side — near to 147C.

(4) *Shape.*—Pointed, acuminate.

(5) *Texture.*—Upper side is leathery and under side is matte.

(6) *Edge.*—Serrate.

(7) *Serration.*—Ordinary.

(8) *Leaf stem.*—Color — light green. Under side — light green.

(9) Stipules.—Medium length.

(10) *Resistance to disease.*—Blackspot — Average. Mildew — Above average. Rust — Above average.

D. Wood:

(1) *New wood.*—Color — light green. Bark — smooth.

(2) *Old wood.*—Color — dark green. Bark — smooth.

E. Thorns:

(1) *Thorns.*—Quantity (main stalk) — ordinary. On laterals from stalk — average. Form — thin, slight recurve. Length — medium. Color — reddish tan to greenish brown. Position — Irregular.

F. Winter hardiness: Needs protection in severe climates.

I claim:

1. A new and distinct variety of rose plant of the hybrid tea class, substantially as shown and described, characterized particularly by attractive deep red flowers which are long lasting on the plant and after cutting.

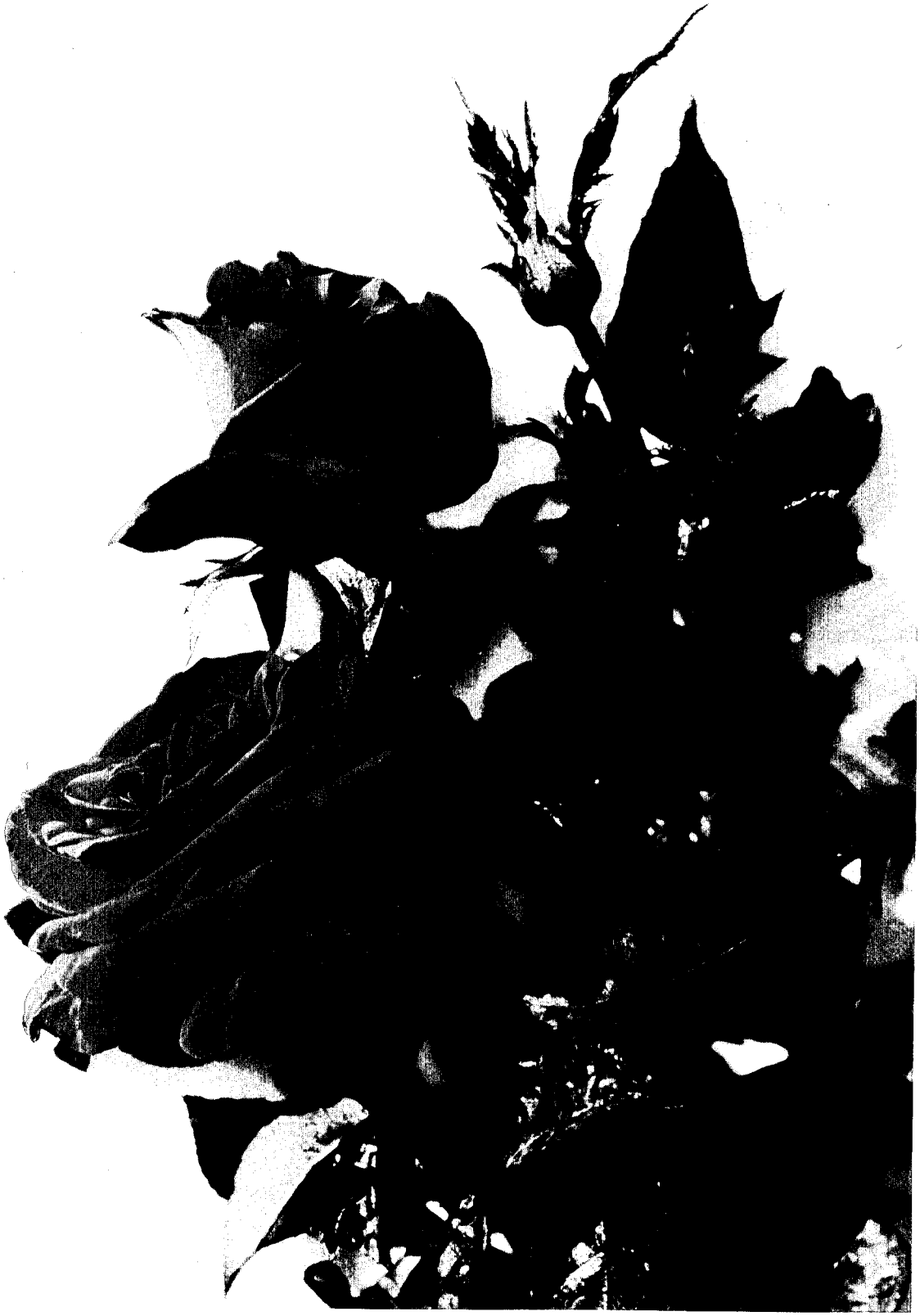

* * * * *